US012385056B2

(12) United States Patent
Hwang et al.

(10) Patent No.: US 12,385,056 B2
(45) Date of Patent: Aug. 12, 2025

(54) METHOD FOR MASS PRODUCTION OF TARGET PROTEIN IN PLANT

(71) Applicants: POSTECH ACADEMY-INDUSTRY FOUNDATION, Gyeongsangbuk-do (KR); BioApplications Inc., Gyeongsangbuk-do (KR)

(72) Inventors: In Hwan Hwang, Gyeongsangbuk-do (KR); Hyang Ju Kang, Gyeongsangbuk-do (KR); Jun Ho Lee, Gyeongsangbuk-do (KR); Shijian Song, Gyeongsangbuk-do (KR); Selvan Thangarasu Muthamil, Gyeongsangbuk-do (KR)

(73) Assignees: POSTECH ACADEMY-INDUSTRY FOUNDATION, Gyeongsangbuk-do (KR); BioApplications Inc., Gyeongsangbuk-do (KR)

( * ) Notice: Subject to any disclaimer, the term of this patent is extended or adjusted under 35 U.S.C. 154(b) by 0 days.

(21) Appl. No.: 17/912,835

(22) PCT Filed: Feb. 1, 2021

(86) PCT No.: PCT/KR2021/001283
§ 371 (c)(1),
(2) Date: Sep. 19, 2022

(87) PCT Pub. No.: WO2021/187750
PCT Pub. Date: Sep. 23, 2021

(65) Prior Publication Data
US 2023/0113417 A1   Apr. 13, 2023

(30) Foreign Application Priority Data
Mar. 20, 2020 (KR) .................. 10-2020-0034576

(51) Int. Cl.
*C12N 15/82* (2006.01)

(52) U.S. Cl.
CPC ..... *C12N 15/8257* (2013.01); *C12N 15/8205* (2013.01)

(58) Field of Classification Search
None
See application file for complete search history.

(56) References Cited

FOREIGN PATENT DOCUMENTS

| CN | 110511941 | 11/2019 | |
|---|---|---|---|
| EP | 1544300 | 6/2005 | |
| KR | 10-2012-0055831 | 6/2012 | |
| KR | 1020140035735 A | * 3/2014 | ......... C12N 15/8251 |
| KR | 10-2018-0084680 | 9/2019 | |
| KR | 10-2019-0030263 | 2/2020 | |
| WO | WO 2009/062253 | 5/2009 | |
| WO | WO 2013/012729 | 1/2013 | |

OTHER PUBLICATIONS

Virlouvet et al., ABA signaling is necessary but not sufficient for RD29B transcriptional memory during successive dehydration stresses in Arabidopsis thaliana, 2014, The Plant Journal, vol. 79(1), pp. 150-161 (Year: 2014).*
GenBank Accession D13044, *Arabidopsis thaliana* DNA for RD29B, RD29A, complete cds, Nov. 20, 2004 (Year: 2004).*
GenBank Accession NC_001497.2 Cauliflower mosaic virus, complete genome, Aug. 13, 2018 (Year: 2018).*
Deaner et al., Promoter and Terminator Discovery and Engineering, 2016, Synthetic Biology-Metabolic Engineering, Advances in Biochemical Engineering/Biotechnology, vol. 162, pp. 1-24 (Year: 2016).*
Matsuyama, T., Recent developments in terminator technology in *Saccharomyces cerevisiae*, 2019, Journal of Bioscience and Bioengineering, vol. 128(6), pp. 655-661 (Year: 2019).*
Comai et al., Novel and useful properties of a chimeric plant promoter combining CaMV 35S and MAS elements, 1990, Plant Molecular Biology, vol. 15, pp. 373-381 (Year: 1990).*
Arzola et al., "Transient Co-Expression of Post-Transcriptional Gene Silencing Suppressors for Increased in Planta Expression of a Recombinant Anthrax Receptor Fusion Protein," Int J Mol Sci (2011) 12:4975-4990.
Comai et al., "Novel and useful properties of a chimeric plant promoter combining CaMV 35S and MAS elements," Plant Molecular Biology (1990) 15:373-381.
Fischer et al., "Molecular Farming of Recombinant Antibodies in Plants," Biol Chem (1999) 380:825-839.
Garabagi et al., "Utility of the P19 suppressor of gene-silencing protein for production of therapeutic antibodies in Nicotiana expression hosts," Plant Biotechnology Journal (2012) 1-11.

(Continued)

*Primary Examiner* — Bratislav Stankovic
*Assistant Examiner* — Christina L Meadows
(74) *Attorney, Agent, or Firm* — Morrison & Foerester LLP

(57) ABSTRACT

The present invention relates to a method for mass-producing a target protein in a plant and, more specifically, to a method for producing high levels of protein in plant leaf cells, in which an expression cassette construct for high expression of a target gene and an expression cassette construct for high expression of p38 as a gene silencing suppressor, are prepared, a binary vector for transient expression in plant cells, having the construct together, is then prepared, and the binary vector is then subjected to *agrobacterium*-mediated transformation by using a single *agrobacterium* culture.

12 Claims, 7 Drawing Sheets

Specification includes a Sequence Listing.

(56) References Cited

OTHER PUBLICATIONS

GenBank Accession No. D13044.1 (Nov. 20, 2004) "*Arabidopsis thaliana* DNA for RD29B, RD29A, complete cds," Retrieved Apr. 21, 2021.
GenBank Accession No. NC_001497.2 (Aug. 13, 2018) "Cauliflower mosaic virus, complete genome," Retrieved Apr. 21, 2021.
Hanahan et al., "Studies on transformation of *Escherichia coli* with Plasmids," J Mol Biol (1983) 166:557-580.
Holtz et al., "Commercial-scale biotherapeutics manufacturing facility for plant-made pharmaceuticals," Plant Biotechnology Journal (2015) 13:1180-1190.
Marusic et al., "Production of an active anti-CD20-hIL-2 immunocytokine in Nicotiana benthamiana," Plant Biotechnology Journal (2015) 1-12.
Regnard et al., "High level protein expression in plants through the use of a novel autonomously replicating geminivirus shuttle vector," Plant Biotechnology Journal (2010) 8:38-46.
Staub et al., "High-yield production of a human therapeutic protein in tobacco chloroplasts," Nature Biotechnology (2000) 18:333-338.
Virlouvet et al., "ABA signaling is necessary but not sufficient for RD29B transcriptional memory during successive dehydration stresses in *Arabidopsis thaliana*," The Plant Journal (2014) 79:150-161.
Werner et al., "High-level recombinant protein expression in transgenic plants by using a double-inducible viral vector," PNAS (2011) 108(34):14061-14066.
Shoji et al., "A plant-produced H1N1 trimeric hemagglutinin protects mice from a lethal influenza virus challenge," Human Vaccines & Immunotherapeutics (Mar. 18, 2019), vol. 9, No. 3, p. 553-560.
Yamamoto et al., "Improvement of the transient expression system for production of recombinant proteins in plants," Scientifics Reports (Mar. 19, 2018), vol. 8, No. 1, p. 1-10.

* cited by examiner

[FIG. 1]
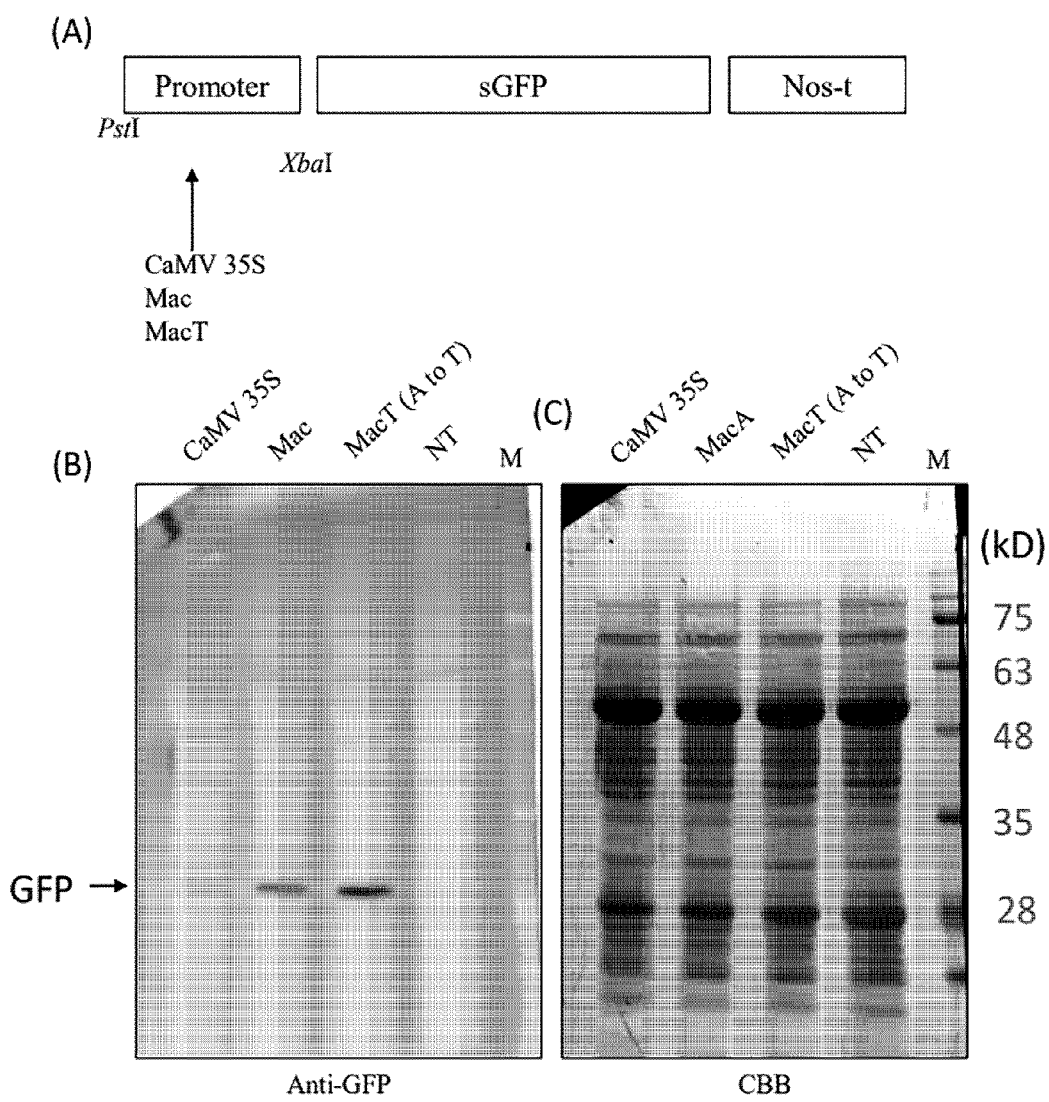

[FIG. 2]
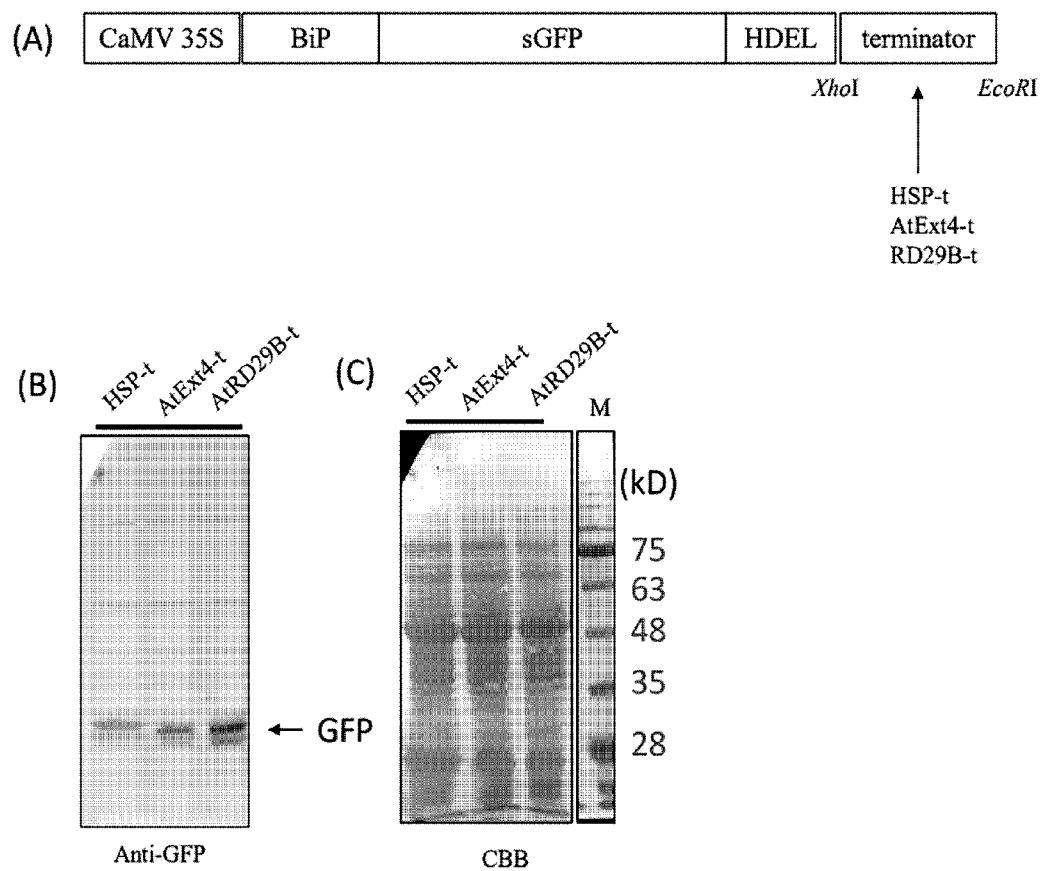

[FIG. 3]
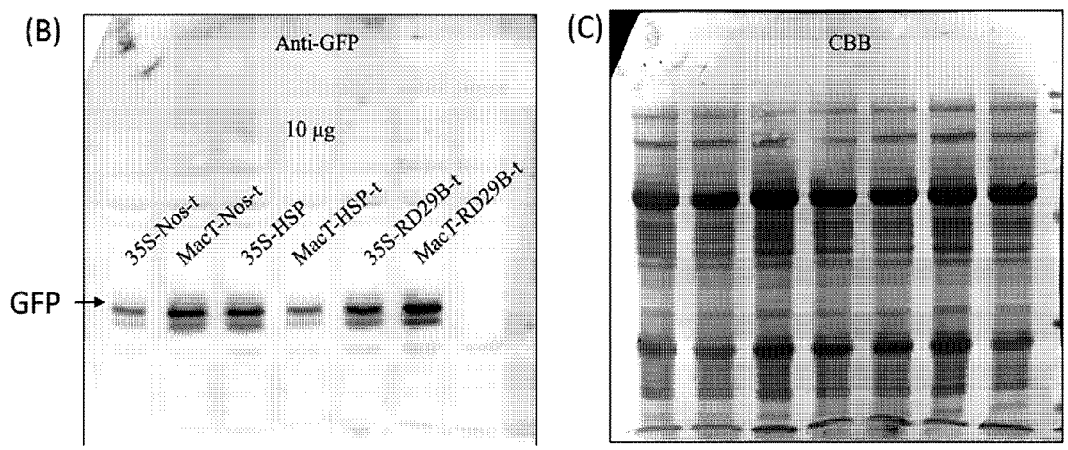

[FIG. 4]
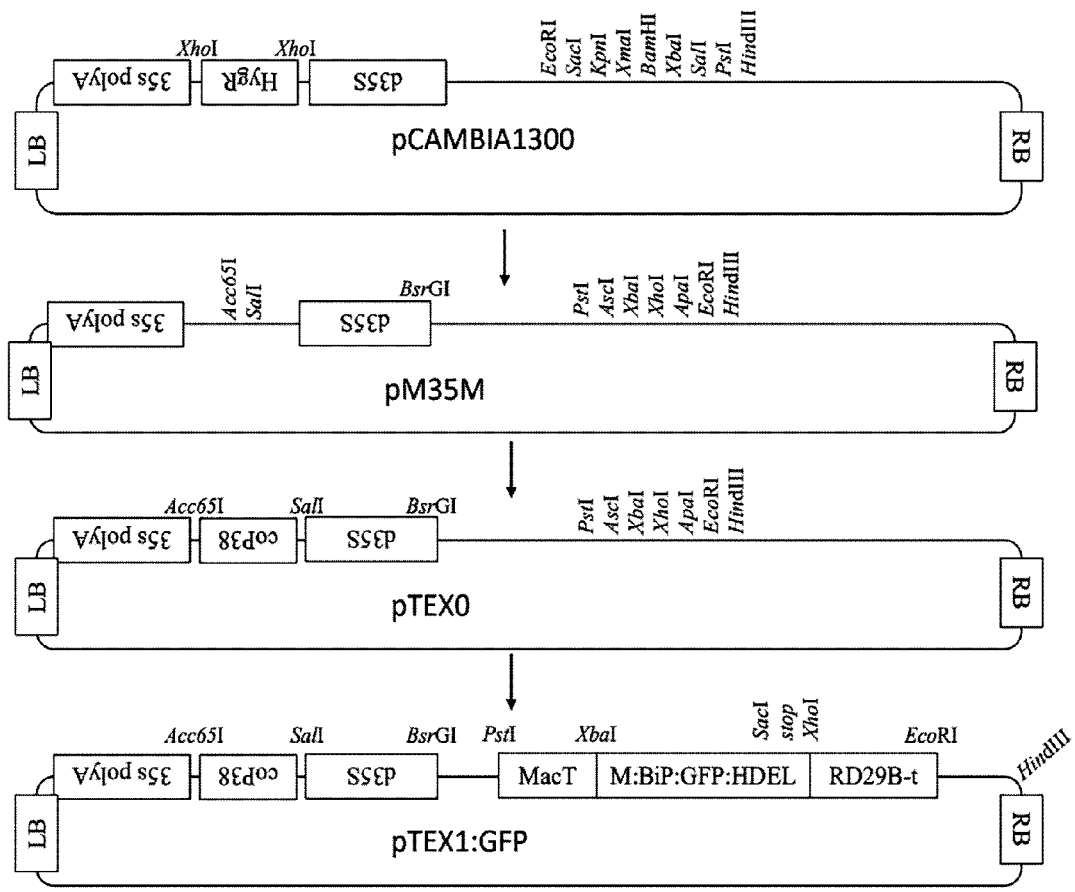

[FIG. 5]
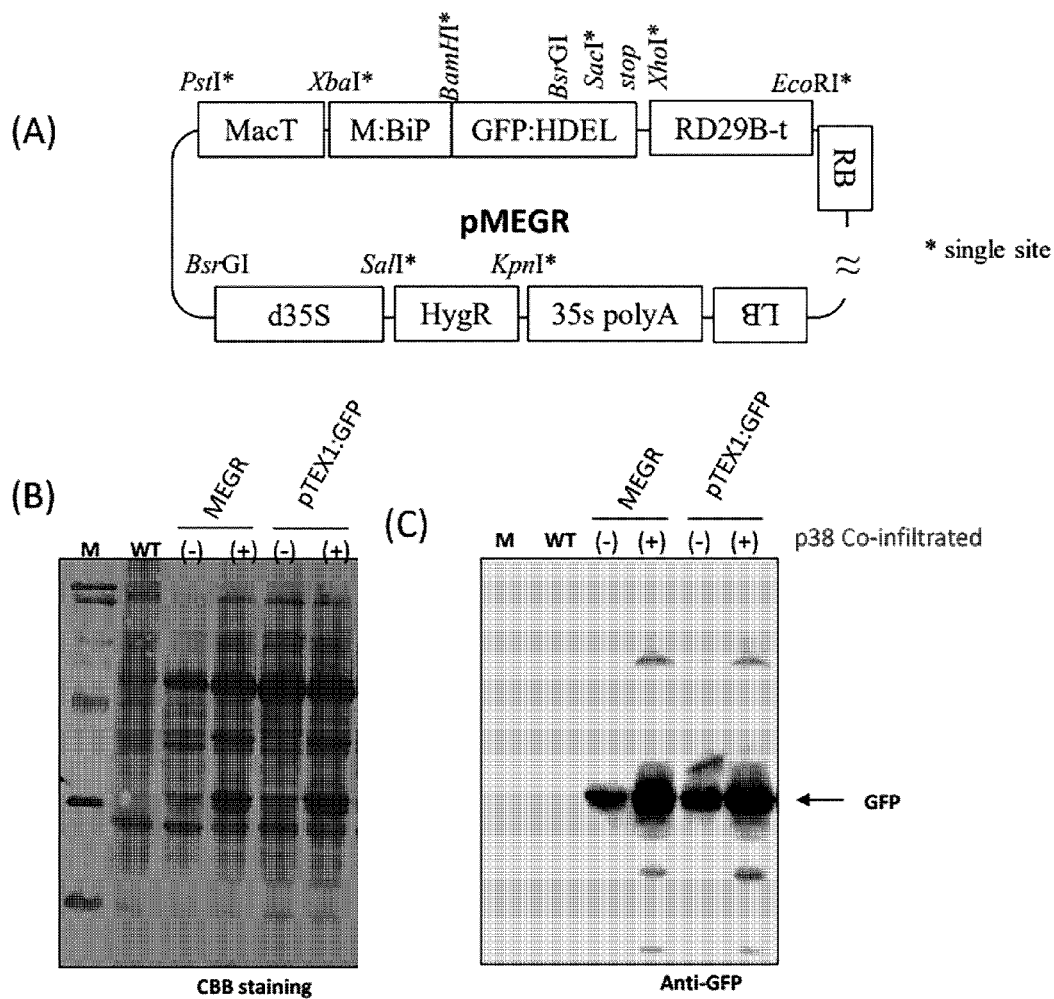

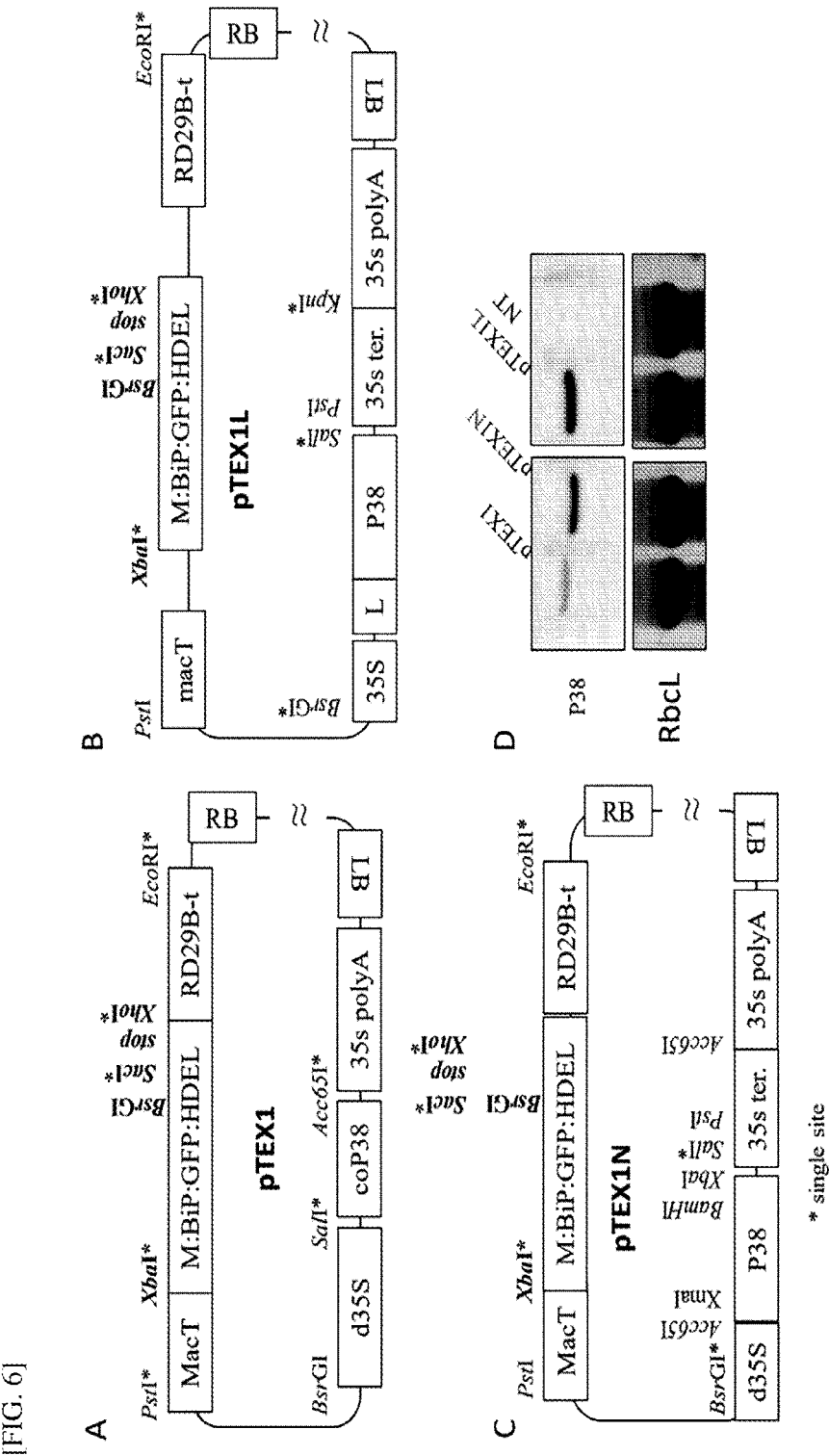
[FIG. 6]

[FIG. 7]
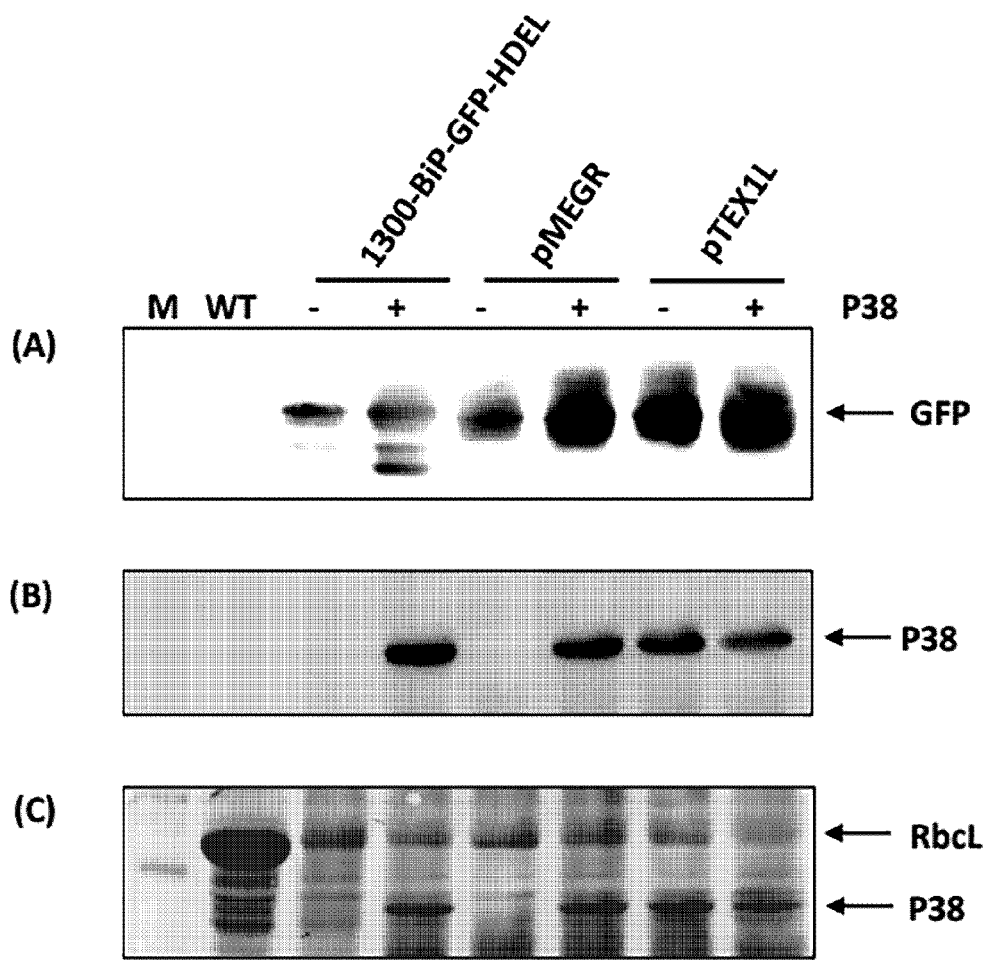

SEQUENCE LISTING

```
<160> NUMBER OF SEQ ID NOS: 12

<210> SEQ ID NO 1
<211> LENGTH: 1220
<212> TYPE: DNA
<213> ORGANISM: Artificial
<220> FEATURE:
<223> OTHER INFORMATION: Mac promoter

<400> SEQUENCE: 1
agagatctcc tttgccccag agatcacaat ggacgacttc ctctatctct acgatctagt      60
caggaagttc gacggagaag gtgacgatac catgttcacc actgataatg agaagattag     120 cctttcaat ttcagaaaga atgctaaccc acagatggtt agagaggctt acgcagcagg     180
tctcatcaag acgatctacc cgagcaataa tctccaggag atcaaatacc ttcccaagaa     240
ggttaaagat gcagtcaaaa gattcaggac taactgcatc aagaacacag agaaagatat     300
atttctcaag atcagaagta ctattccagt atggacgatt caaggcttgc ttcacaaacc     360
aaggcaagta atagagattg gagtctctaa aaaggtagtt cccactgaat caaaggccat     420
ggagtcaaag attcaaatag aggacctaac agaactcgcc gtaaagactg gcgaacagtt     480
catacagagt ctcttacgac tcaatgacaa gaagaaaatc ttcgtcaaca tggtggagca     540
cgacacgctt gtctactcca aaaatatcaa agatacagtc tcagaagacc aaagggcaat     600
tgagactttt caacaagggg taatatccgg aaacctcctc ggattccatt gcccagctat     660
```

```
ctgtcacttt attgtgaaga tagtggaaaa ggaaggtggc tcctacaaat gccatcattg    720
cgataaagga aaggccatcg ttgaagatgc ctctgccgac agtggtccca aagatggacc    780
cccacccacg aggagcatcg tggaaaaaga agacgttcca accacgtctt caaagcaagt    840
ggattgatgt gacgcaagac gtgacgtaag tatctgagct agttttatt tttctactaa     900 tttggtcgtt tatttcggcg tgtaggacat ggcaaccggg cctgaatttc gcgggtattc    960
tgtttctatt ccaactttt cttgatccgc agccattaac gacttttgaa tagatacgct    1020
gacacgccaa gcctcgctag tcaaaagtgt accaaacaac gctttacagc aagaacggaa   1080
tgcgcgtgac gctcgcggtg acgccatttc gccttttcag aaatggataa atagccttgc   1140
ttcctattat atcttcccaa attaccaata cattacacta gcatctgaat ttcataacca   1200
atctcgatac accaaatcga                                                1220

<210> SEQ ID NO 2
<211> LENGTH: 1220
<212> TYPE: DNA
<213> ORGANISM: Artificial
<220> FEATURE:
<223> OTHER INFORMATION: Mac T promoter

<400> SEQUENCE: 2
agagatctcc tttgccccag agatcacaat ggacgacttc ctctatctct acgatctagt     60
caggaagttc gacggagaag gtgacgatac catgttcacc actgataatg agaagattag    120
ccttttcaat ttcagaaaga atgctaaccc acagatggtt agagaggctt acgcagcagg    180
tctcatcaag acgatctacc cgagcaataa tctccaggag atcaaatacc ttcccaagaa    240
ggttaaagat gcagtcaaaa gattcaggac taactgcatc aagaacacag agaaagatat    300
atttctcaag atcagaagta ctattccagt atggacgatt caaggcttgc ttcacaaacc    360
aaggcaagta atagagattg gagtctctaa aaaggtagtt cccactgaat caaaggccat    420
ggagtcaaag attcaaatag aggacctaac agaactcgcc gtaaagactg gcgaacagtt    480
catacagagt ctcttacgac tcaatgacaa gaagaaaatc ttcgtcaaca tggtggagca    540
cgacacgctt gtctactcca aaaatatcaa agatacagtc tcagaagacc aaagggcaat    600
tgagactttt caacaagggg taatatccgg aaacctcctc ggattccatt gcccagctat    660
ctgtcacttt attgtgaaga tagtggaaaa ggaaggtggc tcctacaaat gccatcattg    720
cgataaagga aaggccatcg ttgaagatgc ctctgccgac agtggtccca aagatggacc    780
cccacccacg aggagcatcg tggaaaaaga agacgttcca accacgtctt caaagcaagt    840
ggattgatgt gacgcaagac gtgacgtaag tatctgagct agttttatt tttctactaa     900 tttggtcgtt tatttcggcg tgtaggacat ggcaaccggg cctgaatttc gcgggtattc    960
tgtttctatt ccaactttt cttgatccgc agccattaac gacttttgaa tagatacgct    1020
gacacgccaa gcctcgctag tcaaaagtgt accaaacaac gctttacagc aagaacggaa   1080
tgcgcgtgac gctcgcggtg acgccatttc gccttttcag aaatggataa atagccttgc   1140
ttcctattat atcttcccaa attaccaata cattacacta gcatctgaat ttcataacca   1200
atctcgatac accaaatcgt                                                1220

<210> SEQ ID NO 3
<211> LENGTH: 520
<212> TYPE: DNA
<213> ORGANISM: Artificial
<220> FEATURE:
```

<223> OTHER INFORMATION: RD29B terminator

<400> SEQUENCE: 3

```
aattttactc aaaatgtttt ggttgctatg gtagggacta tggggttttc ggattccggt    60
ggaagtgagt ggggaggcag tggcggaggt aagggagttc aagattctgg aactgaagat   120
ttggggtttt gcttttgaat gtttgcgttt ttgtatgatg cctctgtttg tgaactttga   180
tgtattttat ctttgtgtga aaagagatt gggttaataa aatatttgct ttttggata    240
agaaactctt ttagcggccc attaataaag gttacaaatg caaaatcatg ttagcgtcag   300
atatttaatt attcgaagat gattgtgata gatttaaaat tatcctagtc aaaaagaaag   360
agtaggttga gcagaaacag tgacatctgt tgtttgtacc atacaaatta gtttagatta   420
ttggttaaca tgttaaatgg ctatgcatgt gacatttaga ccttatcgga attaatttgt   480
agaattatta attaagatgt tgattagttc aaacaaaaat                         520
```

<210> SEQ ID NO 4
<211> LENGTH: 1025
<212> TYPE: DNA
<213> ORGANISM: Artificial
<220> FEATURE:
<223> OTHER INFORMATION: BiP-sGFP-HDEL

<400> SEQUENCE: 4

```
atggctcgct cgtttggagc taacagtacc gttgtgttgg cgatcatctt cttcggtgag    60
tgatttccg atcttcttct ccgatttaga tctcctctac attgttgctt aatctcagaa   120
cctttttcg ttgttcctgg atctgaatgt gtttgtttgc aatttcacga tcttaaaagg   180
ttagatctcg attggtattg acgattggaa tctttacgat ttcaggatgt ttatttgcgt   240
tgtcctctgc aatagaagag gctacgaagt taaggatcca agatgatgat gataaggtga   300
gcaagggcga ggagctgttc accggggtgg tgcccatcct ggtcgagctg gacggcgacg   360
taaacggcca caagttcagc gtgtccggcg agggcgaggg cgatgccacc tacggcaagc   420
tgaccctgaa gttcatctgc accaccggca agctgcccgt gccctggccc accctcgtga   480
ccaccttcac ctacggcgtg cagtgcttca gccgctaccc cgaccacatg aagcagcacg   540
acttcttcaa gtccgccatg cccgaaggct acgtccagga gcgcaccatc ttcttcaagg   600
acgacggcaa ctacaagacc cgcgccgagt gaagttcga gggcgacacc ctggtgaacc   660
gcatcgagct gaagggcatc gacttcaagg aggacggcaa catcctgggg cacaagctgg   720
agtacaacta caacagccac aacgtctata tcatggccga caagcagaag aacggcatca   780
aggtgaactt caagatccgc cacaacatcg aggacggcag cgtgcagctc gccgaccact   840
accagcagaa cacccccatc ggcgacggcc ccgtgctgct gcccgacaac cactacctga   900
gcacccagtc cgccctgagc aaagacccca acgagaagcg cgatcacatg gtcctgctgg   960
agttcgtgac cgccgccggg atcactctcg gcatggacga gctgtacaag cacgatgagc  1020
tctag                                                             1025
```

<210> SEQ ID NO 5
<211> LENGTH: 272
<212> TYPE: DNA
<213> ORGANISM: Artificial
<220> FEATURE:
<223> OTHER INFORMATION: BiP

<400> SEQUENCE: 5

```
atggctcgct cgtttggagc taacagtacc gttgtgttgg cgatcatctt cttcggtgag    60
```

```
tgattttccg atcttcttct ccgatttaga tctcctctac attgttgctt aatctcagaa      120 cctttttcg ttgttcctgg atctgaatgt gtttgtttgc aatttcacga tcttaaaagg       180
ttagatctcg attggtattg acgattggaa tctttacgat ttcaggatgt ttatttgcgt      240
tgtcctctgc aatagaagag gctacgaagt ta                                    272
```

<210> SEQ ID NO 6
<211> LENGTH: 21
<212> TYPE: DNA
<213> ORGANISM: Artificial
<220> FEATURE:
<223> OTHER INFORMATION: 5' UTR, M

<400> SEQUENCE: 6

```
ggcgtgtgtg tgtgttaaag a                                                21
```

<210> SEQ ID NO 7
<211> LENGTH: 714
<212> TYPE: DNA
<213> ORGANISM: Artificial
<220> FEATURE:
<223> OTHER INFORMATION: sGFP

<400> SEQUENCE: 7

```
gtgagcaagg gcgaggagct gttcaccggg gtggtgccca tcctggtcga gctggacggc      60
gacgtaaacg gccacaagtt cagcgtgtcc ggcgagggcg agggcgatgc cacctacggc      120
aagctgaccc tgaagttcat ctgcaccacc ggcaagctgc ccgtgccctg gcccaccctc      180
gtgaccacct tcacctacgg cgtgcagtgc ttcagccgct accccgacca catgaagcag      240
cacgacttct tcaagtccgc catgcccgaa ggctacgtcc aggagcgcac catcttcttc      300
aaggacgacg gcaactacaa gacccgcgcc gaggtgaagt tcgagggcga cacccctggtg     360 aaccgcatcg agctgaaggg catcgacttc aaggaggacg gcaacatcct ggggcacaag      420
ctggagtaca actacaacag ccacaacgtc tatatcatgg ccgacaagca gaagaacggc      480
atcaaggtga acttcaagat ccgccacaac atcgaggacg gcagcgtgca gctcgccgac      540
cactaccagc agaacacccc catcggcgac ggccccgtgc tgctgcccga caaccactac      600
ctgagcaccc agtccgccct gagcaaagac cccaacgaga agcgcgatca catggtcctg      660
ctggagttcg tgaccgccgc cgggatcact ctcggcatgg acgagctgta caag            714
```

<210> SEQ ID NO 8
<211> LENGTH: 12
<212> TYPE: DNA
<213> ORGANISM: Artificial
<220> FEATURE:
<223> OTHER INFORMATION: HDEL

<400> SEQUENCE: 8

```
cacgatgagc tc                                                          12
```

<210> SEQ ID NO 9
<211> LENGTH: 1056
<212> TYPE: DNA
<213> ORGANISM: Artificial
<220> FEATURE:
<223> OTHER INFORMATION: P38

<400> SEQUENCE: 9

```
atggaaaatg atcctagagt ccggaagttc gcatctgatg gcgcccaatg ggcgataaag      60
```

```
tggcagaaga agggctggtc aaccctaacc agcagacaga aacagaccgc ccgcgcagcg    120
atggggatca agctctctcc tgtggcgcaa cctgtgcaga aagtgactcg actgagtgct    180
ccggtggccc ttgcctaccg cgaggttacc acccagcctc gggtctctac tgccagggac    240
ggcataacca gaagcggttc tgaactgatc acaaccttga agaagaacac tgacactgaa    300
cctaagtaca ccacagctgt gcttaaccca agcgaacccg aacattcaa ccagctcatt     360 aaggaggcgg cccagtatga aaataccga ttcacgtcac tcagatttag gtactccccc     420 atgagcccctt caaccaccgg aggcaaggtg gctctggcat tcgatcgaga tgccgccaaa   480
cctccgccca acgacctcgc ttccctctac aacatagagg gttgtgtatc tagcgtgccc    540
tggacagggt ttattttgac cgtcccaaca gattctactg accgctttgt ggcggatggt    600
atcagcgatc caaagcttgt cgatttcggc aagcttatca tggccaccta cggccaagga    660
gccaatgatg ccgcccaact cggtgaagtg cgagtcgagt acaccgtgca gctcaagaac    720
agaactggct caaccagcga cgcccagatt ggggacttcg caggtgttaa ggacggaccc    780
aggctggttt catggtccaa gaccaagggg acagctgggt gggagcacga ttgtcatttt    840
ctcggaaccg gaaacttctc gttgacattg ttctacgaga aggcgccggt ctcggggcta    900
gaaaacgcag acgcctctga cttctcggtc ctgggagaag ccgcagcagg tagtgtccaa    960
tgggcaggag tgaaggtagc agaaagggga caaggcgtga aaatggtcac aactgaggag   1020
cagccaaagg gtaaatggca agcactcaga atttag                             1056

<210> SEQ ID NO 10
<211> LENGTH: 21
<212> TYPE: DNA
<213> ORGANISM: Artificial
<220> FEATURE:
<223> OTHER INFORMATION: L 5'-UTR

<400> SEQUENCE: 10
attattacat caaaacaaaa a                                              21

<210> SEQ ID NO 11
<211> LENGTH: 4
<212> TYPE: PRT
<213> ORGANISM: Artificial Sequence
<220> FEATURE:
<223> OTHER INFORMATION: synthetic

<400> SEQUENCE: 11

His Asp Glu Leu
1

<210> SEQ ID NO 12
<211> LENGTH: 21
<212> TYPE: DNA
<213> ORGANISM: Artificial Sequence
<220> FEATURE:
<223> OTHER INFORMATION: synthetic construct

<400> SEQUENCE: 12
attattacat caaaacaaaa a                                              21
```

METHOD FOR MASS PRODUCTION OF TARGET PROTEIN IN PLANT

CROSS REFERENCE TO RELATED APPLICATIONS

The present application is a national stage application under 35 U.S.C. § 371 of International Application No. PCT/KR2021/001283, filed internationally on Feb. 1, 2021, which claims priority to Korean Patent Application No. 10-2020-0034576, filed Mar. 20, 2020, the entire contents of which are incorporated herein for all purposes by this reference.

INCORPORATION BY REFERENCE OF SEQUENCE LISTING

The present application is being filed along with a Sequence Listing in electronic format. The Sequence Listing is provided as a file entitled 717572006800SubSeqList.TXT, created Dec. 20, 2023, which is 9,767 bytes in size. The information in the electronic format of the Sequence Listing is incorporated by reference in its entirety.

TECHNICAL FIELD

The present invention relates to a method for mass production of a target protein in a plant, and more particularly, to a method for producing high levels of a target protein in a plant leaf by preparing an expression cassette construct for high expression of a target gene and an expression cassette construct for high expression of p38 as a gene silencing suppressor, and then, preparing a binary vector for transient expression in the plant cells having the construct together, and then applying *agrobacterium*-mediated transformation to the binary vector using a single *agrobacterium* culture.

BACKGROUND ART

Recently, the possibility of low-cost production of recombinant proteins in plants has been proposed, and various attempts have been made therefor (Schillberg et al., 2003; Holtz et al., 2015; Marusic et al., 2016). In particular, studies are underway to confirm the production potential of various medical proteins. The production of recombinant proteins in plants can have various advantages, one of which is that there are almost no toxins such as endotoxins present in microorganisms such as *E. coli*, and there are no pathogens that can infect the human body. In addition, it is known that there are no harmful proteins such as prions, so it is possible to produce recombinant proteins in plants that are safer than recombinant proteins in animal cells or microorganisms. In addition, in terms of manufacturing cost, it is very cheap to grow plants than to grow animal cells, and it is more economical than cultivating microorganisms such as *E. coli* in large-scale production according to the method of cultivating plants. Among them, the first and most important technology is the development of an expression vector capable of inducing high gene expression in plants (Staub et al, 2000; Regnard et al., 2010). In plants, gene expression can be induced through various methods. Various methods are possible, such as a method of integrating a recombinant gene into the genome of a plant, a method of integrating a recombinant gene into a chloroplast genome, and a method of transiently expressing a gene using *Agrobacterium* (Arzola et al., 2011; Werner. et al., 2011). The method of integrating a recombinant gene into a nuclear genome or chloroplast genome produces proteins in plants basically through the process of securing transformants. On the other hand, when proteins are produced by inducing transient expression of genes by infiltrating *Agrobacterium* into plant tissue, the production process of transformants is not included, so the protein production period is short, and in general, compared to protein production through transformants, it has the advantage of a remarkably high level of production (Arzola et al., 2011). In addition, since expression of other gens can be suppressed by co-infiltration of the expression suppression mechanism of other genes in plants with gene silencing suppressors, it is possible to induce higher levels of protein expression (Garabagi et al., 2011). However, whenever transient expression is desired, an *Agrobacterium* culture introduced with a binary vector containing a target protein and an *Agrobacterium* culture introduced with a binary vector expressing a p38 gene silencing suppressor are separately prepared and mixed in an appropriate ratio to perform co-infiltration, which is disadvantageous. In particular, in the case of culturing two types of *Agrobacterium*, there are limitations in terms of time and economy.

The present invention relates to an expression vector that produces high levels of a protein through transient expression in plants by preparing an expression cassette for high expression of a target gene and introducing p38 as a gene silencing suppressor, which suppresses the inhibition of the expression of the target protein, into one binary vector.

DISCLOSURE

Technical Problem

The present invention relates to a method for mass expression of a target protein in a plant, and relates to a binary vector for expression of a target protein that uses transient expression in a plant to transform the target protein into the plant to produce a high level of a protein of the target gene, and a method for mass expression of the target protein in the plant using the same. In order to solve the above problem, the present inventors have developed an expression cassette for high expression of a target protein and an expression cassette for high expression of p38, a gene silencing suppressor, and a binary vector having the two high expression cassettes (for target protein and p38) together. The inventors have confirmed the high level production of the protein of the target gene by using the binary vector to transfer the target protein and the p38 gene to plant cells using a single *Agrobacterium* culture. Specifically, in order to construct a high expression cassette of the target protein, a single base modification (A to T base substitution) was introduced at the 3' end of the Mac promoter to prepare the MacT promoter with a higher transcription level than the original Mac promoter, and As a result of testing the sequences of various termination sites, it was confirmed that a RD29B termination site was a high-efficiency termination site, and an expression cassette for high expression was prepared using the MacT promoter and the RD29B termination site, as components. In addition, a translation enhancing sequence with 21 base pairs that induces high-efficiency translation was used as a 5'-untranslated region (5'-UTR) immediately upstream of AUG codon of a target protein to increase the level of protein production. In order to increase the expression level of the p38 gene introduced into plant cells by *Agrobacterium* together with the target protein, the translational enhancer sequence of 21-base pair length with high transcription efficiency was introduced into 5'-UTR to increase p38 expression, whereby the efficiency of the silencing suppressor was increased. By replacing the original gene expression cassette and hygromycin expression cassette of pCAMBIA1300 with the two expression cassettes (target protein and p38 gene), the two expression cassettes were introduced to complete a pTEX1L vector. When using this pTEX1L, two types of *Agrobacterium* may be used by mixing the *Agrobacterium* containing the vector for p38 expression and the *Agrobacterium* containing the target protein. Thus, the target protein and the p38 can be transferred simultaneously, without co-infiltration, by one type of *Agrobacterium* with the pTEX1L binary vector. Through this, it was confirmed that there was an effect of inducing high level expression of the protein of the target gene and high-efficiency protein production. Accordingly, an expression vector for dual transfer was completed in which one binary vector was able to simultaneously transfer the target protein and the p38, gene silencing suppressor.

An object of the present invention is to provide a recombinant vector for mass production of a target protein in plants.

Another object of the present invention is to provide a transformant transformed with the recombinant vector.

Still another object of the present invention is to provide a method for mass production of a target protein in a plant, including the steps of:
 (a) constructing the above-described recombinant vector;
 (b) introducing the recombinant vector into a cell to prepare a transformant;
 (c) culturing the transformant;
 (d) infiltrating the cultured transformant into a plant; and
 (e) pulverizing the plant to extract a target protein.

Technical Solution

In order to achieve the above objects, the present invention may prepare a recombinant vector for mass production of a target protein in a plant, including (i) a Mac promoter; (ii) a gene coding a target protein; and (iii) a RD29B-t terminator.

According to a preferred embodiment of the present invention, a sequence of the Mac promoter may include a nucleotide sequence of SEQ ID NO: 1.

According to a preferred embodiment of the present invention, the Mac promoter may be a Mac T promoter in which A, which is a 3' terminal base of the Mac promoter, is substituted with T.

According to a preferred embodiment of the present invention, the Mac T promoter may include a nucleotide sequence of SEQ ID NO: 2.

According to a preferred embodiment of the present invention, the RD29B-t terminator may include a nucleotide sequence of SEQ ID NO: 3.

According to a preferred embodiment of the present invention, the target protein may be any one or more proteins selected from the group consisting of a soluble green fluorescent protein, an antigen, an antibody, an antibody fragment, a structural protein, a regulatory protein, a transcription factor, a toxin protein, a hormone, a hormone analog, a cytokine, an enzyme, an enzyme inhibitor, a transport protein, a receptor, a receptor fragment, a biodefense inducer, a storage protein, a movement protein, an exploitative protein, a growth factor, and a reporter protein.

According to a preferred embodiment of the present invention, the vector may be pCAMBIA1300.

According to a preferred embodiment of the present invention, the recombinant vector may further include a gene silencing suppressor gene.

According to a preferred embodiment of the present invention, the gene silencing suppressor gene may be any one or more selected from the group consisting of p38, P19, HC-Pro and TVA 2b.

Further, the present invention may provide a transformant transformed with the recombinant vector.

According to a preferred embodiment of the present invention, the transformant may be *Agrobacterium*.

Still further, the present invention may provide a method for producing a target protein in a plant, including the following steps of:
 (a) constructing the above-described recombinant vector;
 (b) introducing the recombinant vector into a cell to prepare a transformant;
 (c) culturing the transformant;
 (d) infiltrating the cultured transformant into a plant; and
 (e) pulverizing the plant to extract a target protein.

According to a preferred embodiment of the present invention, the step (d) may further include the step of further infiltrating a transformant in which a recombinant vector containing p38 is introduced into a cell into the plant.

Advantageous Effect

The vector according to the present invention has the effect of increasing the expression level of a protein of a target gene. Particularly, this vector was prepared by introducing a single base modification (base substitution of A to T) at the 3' end of the Mac promoter and linking in the order of the MacT promoter which has a higher transcription level than that of the original Mac promoter, a M domain to increase protein expression, a BiP to induce the high accumulation of ER, a HDEL to induce a high accumulation rate in ER, a RD29B termination site, p38 which is a gene silencing suppressor, and 5'-UTR which is a translation amplification sequence. By transforming the recombinant vector into *Agrobacterium* and then culturing the *Agrobacterium*, there is an effect that a target protein can be produced in a plant with low cost and high efficiency by vacuum infiltration.

DESCRIPTION OF DRAWINGS

FIG. 1 shows a result of comparative analysis of the efficiency of three types of promoters (CaMV 35S, Mac or MacT (a single base substitution from A to T at the 3' end of the Mac promoter)). In FIG. 1, (A) is a cleavage map of the construct used in an experiment, (B) is the result of western blot analysis by introducing the plasmid construct into a protoplast, extracting a protein, and reacting the protein with anti-GFP, (C) is the result of staining the membrane with Coomassie blue: NT, non-transformed control; M, protein size of standard.

FIG. 2 shows a result of comparative analysis of protein production levels according to three types of 3' terminal termination sites (HSP-t, AtExt4-t or RD29B-t). In FIG. 2, (A) is a cleavage map of the construct used in an experiment, which includes an expression cassette prepared by inserting BiP-sGFP-HDEL genes containing BiP, which is an ER targeting signal, a soluble GFP, and a HDEL (encoding the amino acid sequence of SEQ ID NO: 11), which is an ER retention signal, between the promoter and the termination site, (B) is the result of western blot analysis by introducing the plasmid construct into a protoplast, extracting a protein, and reacting the protein with anti-GFP, (C) is the result of staining the membrane with Coomassie blue: NT, non-transformed control; M, protein size of standard.

FIG. 3 shows a result of comparative analysis of protein production levels according to the combination of two types of promoters (CaMV 35S or Mac T) and three types of termination sites (Nos-t, HSP-t or RD29B-t). In FIG. 3, (A) is a cleavage map of the construct used in an experiment, which includes an expression cassette prepared by inserting the BiP-sGFP-HDEL gene including BiP, which is an ER targeting signal, sGFP, and HDEL (encoding the amino acid sequence of SEQ ID NO: 11), which is an ER retention signal, between the promoter and the termination site, (B) is the result of western blot analysis by introducing the plasmid construct into a protoplast, extracting a protein, and reacting the protein with anti-GFP, (C) is the result of staining the membrane with Coomassie blue: NT, non-transformed control; M, protein size of standard.

FIG. 4 shows a schematic diagram showing a process of preparing pTEX1 from pCAMBIA1300 in which a Hygromycin gene was removed from pCAMBIA1300 and Acc65I and SalI restriction sites were introduced at the same time; a BsrGI site was introduced at the 5' end of double 35S promoters to prepare pM35M, and a p38 gene was added to the pM35M using the Acc65I and the SalI; and MacT::BiP:sGFP:HDEL::RD29B-t was introduced into pTEX0 using PstI and EcoRI, with HDEL encoding the amino acid sequence of SEQ ID NO: 11.

FIG. 5 shows a result of comparative analysis of protein production levels according to p38 of pmEGR or pTEX1: GFP. In FIG. 5, (A) is a cleavage map of the construct used in an experiment, which includes an expression vector (pMEGR) having MacT::BiP:sGFP:HDEL:RD29B-t in pCAMBIA1300 as a reference construct, with HDEL encoding the amino acid sequence of SEQ ID NO: 11, (B) is the result of staining the membrane with Coomassie blue by co-infiltration of pMEGR or pTEX1:GFP using *Agrobacterium*, alone or mixture with *Agrobacterium* containing a binary vector expressing P38; inducing the expression of GFP in *Nicotiana benthamiana* leaf tissue; extracting a protein on the 5th day after infiltration; and developing them using SDS-page, and (C) is the result of western blot analysis by reacting the protein with anti-GFP.

FIG. 6 shows a result of comparative analysis of the expression level of P38 proteins using pTEX1, pTEX1N or pTEX1L, wherein pTEX1 has coP38, pTEX1N and pTEX1L have an original p38 gene, and pTEX1L contains a 5' UTR of 21 base pairs with an L sequence before P38. In FIG. 6, (A) is a cleavage map of the pTEX1, pTEX1N or pTEX1L, (B) is the result of confirming the expression level of P38 proteins through Western blot analysis by transforming the pTEX1, pTEXN1 and pTEX1L into *Arabidopsis* protoplasts to induce the expression of P38, and performing the Western blot analysis using an anti-P38 antibody: NT, non-transformed protoplasts. RbcL was used as protein loading controls. The constructs include M::BiP:sGFP: HDEL, with HDEL encoding the amino acid sequence of SEQ ID NO: 11.

FIG. 7 shows a result of comparative analysis of the expression level of a target protein induced by pTEX1L. In FIG. 7, (A) is the result of comparing the expression level of the target proteins by pTEX1L wherein pTEX1L, pMERG, 1300-BiP-GFP-HDEL were introduced into *N. benthamiana* with *Agrobacterium* infiltration, with HDEL encoding the amino acid sequence of SEQ ID NO: 11, and the expression levels of the target proteins were compared. Here, the expression levels of an ER targeted GFP protein, which was the target protein, was compared and analyzed using an anti-GFP antibody according to the presence (+) or absence (−) of co-transformation of P38. (B) is the result of comparative analysis of the expression level of P38, wherein the expression levels of P38 using *N. benthamiana* leaf extract were compared using western blot analysis using an anti-P38 antibody. (C) is the result of comparing the levels of Coomassie blue stained P38 and RbcL, wherein the membrane was stained with Coomassie blue after Western blot analysis to confirm the level of P38 and the level of RbcL used as a loading control.

MODE FOR INVENTION

Hereinafter, the present invention will be described in more detail.

As described above, the production of proteins using animal cells or microorganisms causes problems such as various contaminants such as viruses, cancer genes, and enterotoxins, and has disadvantages in that a large amount of time and cost is consumed when mass-produced. In order to overcome these problems, a method for producing a protein in a plant has been developed, but this also has a disadvantage in that the protein expression is low.

Accordingly, the present inventors prepared a recombinant vector for increasing an expression level of a target protein in plants. The recombinant vector of the present invention includes a target protein, and it was confirmed that the protein expression of a target gene in a plant increased to a high level by culturing the recombinant vector containing the target protein and infiltrating the cultured transformant into the plant.

Hereinafter, with reference to the accompanying drawings, embodiments of the present invention will be described in detail so that those of ordinary skill in the art to which the present invention pertains can easily implement them. The present invention may be embodied in many different forms and is not limited to the embodiments described herein.

The present invention relates to providing a recombinant vector for mass production of a target protein in a plant, including (i) a Mac promoter; (ii) a gene encoding a target protein; and (iii) a RD29B-t terminator.

The present inventors tried to develop a high expression promoter with higher expression than the expression of a CaMV 35S promoter, or a 35S promoter having a double enhancer, which is included in a high expression binary vector. Accordingly, after designing a vector containing the CaMV 35S promoter, a Mac promoter (SEQ ID NO: 1), and a Mac T promoter (SEQ ID NO: 2) in which A, which is the 3' terminal base of the Mac promoter sequence, was substituted with T, GFP was expressed. As a result, it was confirmed that the Mac T promoter had a high expression efficiency of about 50% (FIG. 1).

The gene sequence of the Mac promoter may include the nucleotide sequence of SEQ ID NO: 1, specifically, the gene may include a nucleotide sequence having 70% or more, more preferably 80% or more, still more preferably 90% or more, most preferably 95% or more sequence homology to the nucleotide sequence of SEQ ID NO: 1, respectively. The "% sequence homology" for a polynucleotide is identified by comparing comparative regions between two optimally aligned sequences, and part of the polynucleotide sequence within the comparative regions may include an addition or a deletion (i.e., a gap) compared to the reference sequence (without any addition or deletion) for the optimum arrangement of the two sequences.

The Mac promoter may be Mac Tin which A, which is the 3' terminal base of the Mac promoter, is substituted with T, and the Mac T promoter may include the nucleotide sequence of SEQ ID NO: 2, specifically, the gene may include the nucleotide sequences having 70% or more, more preferably 80% or more, still more preferably 90% or more, and most preferably 95% or more sequence homology to the nucleotide sequence of SEQ ID NO: 2, respectively. The "% sequence homology" for a polynucleotide is identified by comparing comparative regions between two optimally aligned sequences, and part of the polynucleotide sequence within the comparative regions may include an addition or a deletion (i.e., a gap) compared to the reference sequence (without any addition or deletion) for the optimum arrangement of the two sequences.

For gene expression, the expression level according to the type of termination site was identified. Among the genes of *Arabidopsis thaliana*, the expression of RD29B is usually kept very low, but it is known that when plants are subjected to abiotic stress such as drought, the expression is quickly induced to be high by substances such as ABA. Accordingly, it was identified whether the RD29B termination site (RD29B-t; SEQ ID NO: 3) increased the expression level of this gene under the assumption that the termination site of transcription would also occur with high efficiency in order to rapidly induce high transcription levels of RD29B. Using the AtExt4 termination site (AtExt4-t) of *Arabidopsis thaliana* and the HSP termination site terminator (HSP-t), which are considered to induce high expression, as reference terminators, the expression vector as shown in FIG. 2 was prepared and introduced into the protoplasts of *Arabidopsis thaliana* in order to identify the expression level of sGFP (FIG. 2). As a result, it was confirmed that the RD29B termination site induced more than 50% higher expression of sGFP than the expression by the two reference termination sites.

The RD29B-t termination site may include the nucleotide sequence of SEQ ID NO: 3, and specifically, the gene may include the nucleotide sequences having 70% or more, more preferably 80% or more, still more preferably 90% or more, and most preferably 95% or more sequence homology to SEQ ID NO: 3, respectively. The "% sequence homology" for a polynucleotide is identified by comparing comparative regions between two optimally aligned sequences, and part of the polynucleotide sequence within the comparative regions may include an addition or a deletion (i.e., a gap) compared to the reference sequence (without any addition or deletion) for the optimum arrangement of the two sequences.

The present inventors independently confirmed that each of the MacT promoter and the RD29B termination site (RD29B-t) increased the expression level of the protein of a gene as shown in FIGS. 1 and 2. Accordingly, it was identified whether the combination of the above components still increased the expression level of a protein of a gene. The MacT promoter and the RD29B-t were used as a promoter and a terminator, and BiP-sGFP-HDEL gene (SEQ ID NO: 4) was inserted therebetween to prepare an expression cassette. BiP (SEQ ID NO: 5) was a sequence for targeting an endoplasmic reticulum, GFP (SEQ ID NO: 6) was a nucleotide sequence of a green fluorescent protein, and HDEL (SEQ ID NO: 8; encoding the amino acid sequence of SEQ ID NO: 11) was used as an endoplasmic reticulum retaining nucleotide sequence for retaining a protein in an endoplasmic reticulum. As a reference construct, 35S::Nos-t, MacT::Nos-t, 35S::HSP-t, MacT::HSP-t, 35S::RD29B-t were prepared as shown in FIG. 3. Then, an expression construct was completed using BiP-sGFP-HDEL as a reporter gene. To compare them with MacT::RD29B-t, the expression of GFP was induced using *Arabidopsis* protoplasts and the expression level was identified. As expected, it was confirmed that MacT::RD29B-t showed the highest protein level. The MacT and the RD29B-t were established as the sequences of the promoter and termination sites of a new expression cassette for high expression.

The "target protein", which is a gene coding a foreign product to be expressed, is a gene coding all kinds of proteins capable of being expressed as recombinant proteins. As representative examples, there are an insulin, a cytokine (interleukin, a tumor necrosis factor, interferon, a colony stimulating factor, chemokine, and the like), an erythropoietin, an antigen, an antibody, an antibody fragment, a structural protein, a regulatory protein, a transcription factor, a toxin protein, a hormone, a hormone analog, an enzyme, an enzyme inhibitor, a transport protein, a receptor (e.g., a tyrosine kinase receptor, etc.), a receptor fragment, a biodefense inducer, a storage protein, a movement protein, an exploitative protein, a reporter protein, a growth factor, a viral gene for producing vaccines, a bacterial gene, and the like. The target gene may include a "cloning site", which is a DNA sequence including a recognition or cleavage site of a restriction enzyme introduced therein so as to be integrated into the vector.

By including the BiP signal sequence and the HDEL, which is an ER retention signal, at the N- and C-terminus of the recombinant protein gene, respectively, it can have an effect of inducing accumulation in an endoplasmic reticulum (ER) at a high concentration. The recombinant vector may further include any one selected from the group consisting of a chaperone binding protein (BiP) and a His-Asp-Glu-Leu (HDEL) (SEQ ID NO: 11) peptide, the BiP may include the nucleotide sequence of SEQ ID NO: 5, and the nucleotide sequence encoding HDEL (His-Asp-Glu-Leu) (SEQ ID NO: 11) may include the nucleotide sequence of SEQ ID NO: 8.

In addition, the recombinant vector may further include a 5'-UTR, which is a translation amplification sequence, and the 5'-UTR may include the nucleotide sequence of SEQ ID NO: 6 or SEQ ID NO: 12.

The recombinant refers to a cell which replicates a heterogeneous nucleotide or expresses said nucleotide, or expresses a peptide, a heterogeneous peptide, or a protein encoded by a heterogeneous nucleotide. A recombinant cell can express a gene or a gene fragment in the form of a sense or antisense, which is not found in natural state of cell. In addition, a recombinant cell can express a gene that is found in natural state of cell, provided that said gene is modified and re-introduced into the cell by an artificial means.

The term "recombinant expression vector" means a bacterial plasmid, a phage, a yeast plasmid, a plant cell virus, a mammalian cell virus, or other vectors. Altogether, any plasmid and vector can be used provided that they are capable of replicating and stabilizing in a host. An important feature of the expression vector is having a replication origin, a promoter, a maker gene, and a translation control element. The recombinant expression vector and the expression vector including appropriate transcription/translation control signals can be constructed using methods well known to those skilled in the art. These methods include in vitro recombinant DNA techniques, DNA synthesis techniques, in vivo recombinant techniques, and the like.

A preferred example of the recombinant vector of the present invention is a Ti-plasmid vector which can transfer a part of itself, so called T-region, to a plant cell when the vector is present in an appropriate host. Other types of Ti-plasmid vector are currently used for transferring a hybrid gene to protoplasts that can produce a new plant by appropriately inserting a plant cell or hybrid DNA to a genome of a plant. Especially preferred form of Ti-plasmid vector is a so-called binary vector which has been disclosed in EP 0 120 516 B1 and U.S. Pat. No. 4,940,838. Other vector that can be used for introducing the DNA of the present invention into a host plant can be selected from a double-stranded plant virus (e.g., CaMV), a single-stranded plant virus, and a viral vector which can be originated from Gemini virus, etc., for example a non-complete plant viral vector. Use of the vector can be advantageous especially when a plant host cannot be appropriately transformed.

The high expression of a target protein is induced by using two binary vectors for inducing the expression of a gene silencing suppressor and the expression of the target protein. In the case of protein expression using transient expression, co-expression of a gene silencing suppressor is essential for high expression of the target protein. Accordingly, the two binary vectors are each transformed into *Agrobacterium*, then each *Agrobacterium* culture is made, and the *Agrobacterium* cultures transformed with the vector containing the target protein and the gene silencing suppressor, respectively, are mixed in an appropriate ratio and used for co-infiltration. This requires double the effort and double the cost. Therefore, an expression vector was constructed so that one binary vector simultaneously transfers a target protein and p38, a gene silencing suppressor. As shown in FIG. 4, a tobacco codon optimized p38 (coP38) gene was introduced by substituting the hygromycin gene of pCAMBIA1300 according to the sequence, so that pTEX0 was constructed. Then, MacT::M:BiP:sGFP:HDEL:RD29B-t was introduced to construct pTEX1: GFP. In this case, by having 5'-ggcgtgtgtgtgtgttaaaga-3' (M 5'-UTR, SEQ ID NO: 6) as the 5'-UTR of the immediate upstream region of BiP, high translation efficiency was induced. It was attempted to identify expression using the binary vector for dual transfer for the expression vector constructed in this way. An expression vector (pMEGR) having MacT::BiP:sGFP:HDEL:RD29B-t in pCAMBIA1300 as a reference construct was constructed. The expression level of sGFP was identified by co-infiltration of the two constructs alone or by mixing the two constructs with *Agrobacterium* having p38 (FIG. 5). In the case of pMEGR, it was confirmed that the expression of sGFP was highly induced by co-infiltration of p38. Similarly, in the case of pTEX1, the expression was increased by additional co-infiltration of p38 (FIG. 5). Through this, it was concluded that the amount of p38 expressed by pTEX1 was not sufficient because the expression of sGFP was increased when p38 was co-infiltrated separately even though pTEX1:GFP had p38 intrinsically. It was estimated that the expression amount of p38 might not be sufficient as the T-DNA introduced by the *Agrobacterium* had these two genes at the same time. Therefore, a construct for increasing the expression of p38 included in pTEX1 was reconstructed. A 35S promoter-P38-35S terminator was obtained from pBIN based binary vector (35S: CP in Patent Publication No. 10-2012-0055831) containing the nucleotide sequence of original TCV-CP through PCR, and the corresponding fragment was substituted in pTEX1-EMCC using BsrGI and Acc65I, so that pTEX1N-EMCC was constructed. In addition, in order to further increase the expression level of P38, a method of increasing translation efficiency was employed. This method is considered to be the most efficient method in terms of cellular energy among various methods for increasing the level of protein production. A P38 expression cassette (pTEX1L) was constructed by introducing L:P38 containing the nucleotide sequence of 5'-attattacatcaaaacaaaaa-3' (SEQ ID NO: 12), which is a nucleotide sequence capable of inducing high-efficiency translation, into the 5'-UTR of P38 (FIG. 6). Through this, it was attempted to increase the expression level of P38. After transformation of pTEX1, pTEX1N and pTEX1L into *Arabidopsis* protoplasts, the expression levels of P38 were compared. As a result, the expression level of pTEX1 was the lowest, and the expression level of pTEX1N was about twice the expression level of pTEX1. On the other hand, the expression level of pTEX1L was again about twice higher than the expression level of these pTEX1N ((D) in FIG. 6). Finally, the construct (pTEX1L:sGFP) containing M::BiP:sGFP:HDEL in this pTEX1L was constructed, and the level of expression of the construct was identified. As controls, the pCAMBIA1300 vector containing a 35S promoter-sGFP-HSP terminator and the pMEGR were used, and the controls were compared with the case in which the P38 co-infiltration was performed, respectively. As a result, first, it was confirmed that in transient expression through agro-infiltration in tobacco, as in *Arabidopsis* protoplast transformation, the sGFP expression by the MacT promoter-RD29B termination site was two or three times higher than the expression by the 35S promoter-HSP terminator combination (FIG. 7). In addition, it was confirmed that there was no significant difference between the sGFP expression by the pMEGR with P38 co-infiltration and the sGFP expression by the pTEX1L: sGFP without P38 co-infiltration; also, there was almost no difference in the expression of sGFP even when pTEX1L: sGFP was co-transformed with P38. Through this, an expression vector for dual transfer was completed in which one binary vector can simultaneously transfer the target protein and p38, a gene silencing suppressor.

The vector may be pCAMBIA1300, and the vector (pM35M in FIG. 4) may be prepared by removing a Hygromycin gene from the pCAMBIA1300, and at the same time introducing Acc65I and SalI restriction sites, and introducing a BsrGI site at the 5' end of a double 35S promoter. The vector (pTEX0 in FIG. 4) may be prepared by introducing the P38 gene in the vector (pM35M in FIG. 4) using Acc65I and SalI. The vector (pTEX1 in FIG. 4) may be prepared by further introducing MacT::BiP:sGFP:HDEL::RD29B-t into the vector (pTEX0 in FIG. 4) using PstI and EcoRI.

The recombinant vector may further include a gene silencing suppressor gene. The gene silencing suppressor gene may be any one or more selected from the group consisting of p38, P19, HC-Pro and TVA 2b, preferably, and may further include p38. The p38 may include the nucleotide sequence of SEQ ID NO: 9, and specifically, the gene may include the nucleotide sequences having 70% or more, more preferably 80% or more, still more preferably 90% or more, and most preferably 95% or more sequence homology to SEQ ID NO: 9, respectively. The "% sequence homology" for a polynucleotide is identified by comparing comparative regions between two optimally aligned sequences, and part of the polynucleotide sequence within the comparative regions may include an addition or a deletion (i.e., a gap) compared to the reference sequence (without any addition or deletion) for the optimum arrangement of the two sequences.

The present invention may also provide a transformant transformed with the above described recombinant vector.

In addition, when transforming the vector of the present disclosure into an eukaryotic cell, yeast (*Saccharomyces cerevisiae*), an insect cell, a human cell (e.g., a CHO cell line (Chinese hamster ovary), W138, BHK, COS-7, 293, HepG2, 3T3, RIN, and an MDCK cell line), a plant cell, and the like may be used as a host cell, and the host cell may be preferably *Agrobacterium*.

When a host cell is a prokaryotic cell, a method of delivering the vector of the present disclosure into the host cell may be performed using a CaCl$_2$) method, a method by Hanahan (Hanahan, D., J. Mol. Biol., 166:557-580 (1983)), an electroporation method, and the like. In addition, when the host cell is a eukaryotic cell, the vector may be injected into the host cell by microinjection, calcium phosphate precipitation, electroporation, liposome-mediated transfection, DEAE-dextran treatment, gene bombardment, and the like.

The present invention may also provide a method for producing a target protein in a plant, including the steps of (a) constructing the above-described recombinant vector; (b) introducing the recombinant vector into a cell to prepare a transformant; (c) culturing the transformant; (d) infiltrating the cultured transformant into a plant; and (e) pulverizing the plant to extract a target protein.

In the method for producing a target protein from the transformed plant, the target protein can be obtained by transforming a plant cell with the recombinant vector of the present invention to prepare a transformed cell, and then culturing the transformed cell for an appropriate time so that the target protein can be expressed. In this case, any method known in the art for expressing the target protein can be used.

In step (d) of infiltrating the cultured transformant into a plant, a culture solution of a recombinant vector containing P38 may be simultaneously infiltrated, in addition to the culture solution of the recombinant vector for producing carbonic anhydrase of the present invention. The p38 is a gene silencing suppressor. In addition, there may be gene silencing suppressor P19, HC-Pro, TVA 2b, or the like.

The infiltration into a plant may be performed by a chemical cell method or a vacuum or syringe infiltration method, most preferably a syringe infiltration method, but the present disclosure is not limited thereto.

The plant may be selected from food crops including rice, wheat, barley, corn, soybeans, potatoes, wheats, red beans, oats, and sorghum; vegetable crops including *Arabidopsis*, Chinese cabbage, radish, peppers, strawberries, tomatoes, watermelons, cucumbers, cabbages, melons, pumpkins, green onions, onions, and carrots; special crops including *ginseng*, tobacco, cotton, sesame, sugar cane, sugar beet, *perilla*, peanuts, and rapeseed; fruit trees including apple trees, pear trees, jujube trees, peaches, grapes, citrus fruits, persimmons, plums, apricots, and bananas; flowers including roses, carnations, chrysanthemums, lilies, and tulips.

Although one embodiment of the present invention has been described above, the spirit of the present invention is not limited to the embodiments presented herein, and those skilled in the art who understand the spirit of the present invention will be able to easily suggest other embodiments by adding, changing, deleting, or including components within the scope of the same spirit, but this is also said to be within the scope of the present invention.

[Example 1] Identification of a Promoter with an Optimal Expression Level

As described in FIG. 1, an expression vector was prepared ((A) in FIG. 1). As a promoter, CaMV 35S, Mac, or MacT was introduced. Each of the three types of promoters, soluble green fluorescent protein (sGFP), and a Nos termination site were linked to complete a binary vector for expression. As the backbone of the binary, pCAMBIA1300 was used ((A) in FIG. 1). The binary vector designed as described above was prepared through an overlapping PCR. Each of these constructs was introduced into protoplasts obtained from *Arabidopsis* leaf tissue by electroporation to induce expression. After transformation, the protoplasts were incubated for 2 days at 28° C. in the LB plate containing kanamycin and rifampicin (50 mg/L and 100 mg/L, respectively). After selecting one colony, it was cultured overnight in the LB media containing 5 mL of kanamycin and rifampicin. Proteins were extracted from the protoplasts after 24 hours. Protein extract was prepared using an extraction buffer (50 mM Tris pH 7.5, 150 mM NaCl, 0.1% Triton X100, 2 mM DTT and 1% protease inhibitor cocktail), 5× sample buffer (250 mM Tris-HCl [pH 6.8], 10% SDS, 0.5% bromophenol blue, 50% glycerol v/v, and 500 mM DTT) were added thereto at a final concentration of 1×, thereby preparing an electrophoretic protein sample. The protein extract sample was boiled for 5 minutes, then separated through 10% SDS-PAGE, and then subjected to western blot analysis using an anti-GFP antibody. Through this, the expression level of each of CaMV 35S, Mac, and Mac promoters was comparatively analyzed. As a result, the expression level of the MacT promoter was significantly higher than that of the CaMV 35S promoter, and showed at least 50% higher promoter strength than that of the Mac promoter (FIG. 1).

[Example 2] Identification of a Termination Site with an Optimal Expression Level The expression construct as shown in the schematic diagram of FIG. 2 was prepared. As a promoter, the CaMV 35S was determined, and as a termination site, a HSP termination site, which is known to have high efficiency, an *Arabidopsis* AtExt4 gene termination site, and a RD29B termination site were prepared. An expression cassette was prepared by inserting BiP-sGFP-HDEL genes containing BiP, which is an ER targeting signal, a soluble GFP, and a HDEL, which is an ER retention signal, between the promoter and the termination site, in order to induce expression in the ER and accumulate at a high level. The binary vector designed as described above was prepared through an overlapping PCR. Each of these constructs was introduced into protoplasts obtained from *Arabidopsis* leaf tissue by electroporation to induce expression. After transformation, the protoplasts were incubated for 2 days at 28° C. in the LB plate containing kanamycin and rifampicin (50 mg/L and 100 mg/L, respectively). After selecting one colony, it was cultured overnight in the LB media containing 5 mL of kanamycin and rifampicin. Proteins were extracted from the protoplasts after 24 hours. Protein extract was prepared using an extraction buffer (50 mM Tris pH 7.5, 150 mM NaCl, 0.1% Triton X100, 2 mM DTT and 1% protease inhibitor cocktail), 5× sample buffer (250 mM Tris-HCl [pH 6.8], 10% SDS, 0.5% bromophenol blue, 50% glycerol v/v, and 500 mM DTT) was added thereto at a final concentration of 1×, thereby preparing an electrophoretic protein sample. The protein extract sample was boiled for 5 minutes, then separated through 10% SDS-PAGE, and then subject to western blot analysis using an anti-GFP antibody. The membrane was then stained with Coomassie Blue. As a result, it was confirmed that the RD29B termination site had the highest expression level, among the three types of termination sites (FIG. 2).

Example 3

As shown in FIG. 3, with various combinations of promoters and termination sites, the expression constructs (35S::Nos-t, MacT::Nos-t, 35S::HSP-t, MacT::HSP-t, 35S:: RD29B-t, MacT::RD29B-t) were prepared. An expression cassette was prepared by inserting the BiP-sGFP-HDEL gene (SEQ ID NO: 4) between the promoter and the termination site. The expression cassette was prepared by inserting the BiP-sGFP-HDEL gene including BiP, which is an ER targeting signal, sGFP, and HDEL, which is an ER retention signal, between the promoter and the termination site, in order to induce expression in the ER and accumulate at a high level. The binary vector designed as described above was prepared through an overlapping PCR. Each of these constructs was introduced into protoplasts obtained from *Arabidopsis* leaf tissue by electroporation to induce expression. After transformation, the protoplasts were incubated for 2 days at 28° C. in the LB plate containing kanamycin and rifampicin (50 mg/L and 100 mg/L, respectively). After selecting one colony, it was cultured overnight in the LB media containing 5 mL of kanamycin and rifampicin. Proteins were extracted from the protoplasts after 24 hours. Protein extract was prepared using an extraction buffer (50 mM Tris pH 7.5, 150 mM NaCl, 0.1% Triton X100, 2 mM DTT and 1% protease inhibitor cocktail), 5× sample buffer (250 mM Tris-HCl [pH 6.8], 10% SDS, 0.5% bromophenol blue, 50% glycerol v/v, and 500 mM DTT) was added thereto at a final concentration of 1×, thereby preparing an electrophoretic protein sample. The protein extract sample was boiled for 5 minutes, then separated through 10% SDS-PAGE, and then subject to western blot analysis using an anti-GFP antibody, to identify the level of sGEP. As a result, it was confirmed that the expression of sGFP was highest when the construct had the MacT promoter and the RD29B-t termination site, among the six constructs (FIG. 3). Through this, it was confirmed that the expression cassette having the Mac T promoter and the RD29B-t termination site increased the expression of the protein of the target gene.

[Example 4] Process of Constructing pTEX1:GFP from pCAMBIA1300

An expression vector was constructed so that one binary vector simultaneously transferred the target protein and p38, a gene silencing suppressor. As shown in FIG. 4, the Hygromycin gene was removed from pCAMBIA1300 and Acc65I and SalI restriction sites were introduced at the same time, and a BsrGI site was introduced at the 5' end of the double 35S promoter to prepare pM35M. The tobacco codon optimized p38 (coP38) gene was introduced in the pM35M using the Acc65I and SalI restriction sites to prepare pTEX0. Then, MacT::BiP:sGFP:HDEL::RD29B-t was introduced into the pTEX0 using PstI and EcoRI to construct pTEX1: GFP. In this case, by having 5'-ggcgtgtgtgtgtgttaaaga-3' (M 5'-UTR, SEQ ID NO: 6) as the 5'-UTR of the immediate upstream region of BiP, high translation efficiency was induced.

[Example 5] Vector Map of pMEGR and Comparison of Expression Levels Using the Same Expression was identified using the expression binary vector for double transfer (pTEX1: GFP) constructed in Example 4 above. The expression vector (pMEGR) having MacT::BiP:sGFP:HDEL:RD29B-t in pCAMBIA1300 as a reference construct was constructed. Each of the two types of expression vectors (pTEX1: GFP and pMEGR) was introduced into *Agrobacterium* and cultured. mL of *Agrobacterium* culture medium was added to 50 ml LB culture solution containing kanamycin and rifampicin (50 mg/L and 100 mg/L). After incubation for 16 hours, the *Agrobacterium* was recovered by centrifugation at 4000×g conditions at 28° C. for 8 minutes. The supernatant was discarded and the *Agrobacterium* precipitate was dissolved in an infiltration buffer (10 mM MES, 10 mM MgSO4.7H2O; pH 5.7). The cell concentration was adjusted to 0.8 at OD600 using the infiltration buffer. Then, 400 µM acetosyringone was added to the *Agrobacterium* solution, and left at room temperature for 2 hours. Wild-type *N. benthamiana* was cultured for *Agrobacterium*-mediated infiltration. Seeds of a plant were grown at 24° C., a relative humidity of 40 to 65% under long day conditions (14 h light/10 h dark) with a light intensity of 130 to 150 uE m-2 sec-1. A plant grown for 6 weeks was used for *Agrobacterium*-mediated infiltration. Infiltration with a syringe was performed using a 1 mL syringe without a needle. At the same time, a binary vector containing P38, a gene of the coat protein of a turnip crinkle virus, which is a gene silencing suppression gene, was co-infiltrated. To this end, two types of expression vectors (pTEX1:sGFP and pMEGR) and P38 were introduced into each *Agrobacterium*, and then mixed with an appropriate concentration of *Agrobacterium* culture solution at a ratio of 1:1, followed by infiltration into *N. benthamiana* leaves. On the third day after infiltration, a total protein extract was obtained from *N. benthamiana* leaf tissue, followed by western blot analysis, to identify expression levels. The total protein extract was prepared using an extraction buffer (50 mM Tris pH 7.5, 150 mM NaCl, 0.1% Triton X100, 2 mM DTT and 1% protease inhibitor cocktail), and 5× sample buffer (250 mM Tris-HCl [pH 6.8], 10% SDS, 0.5% bromophenol blue, 50% glycerol v/v, and 500 mM DTT) was added thereto at a final concentration of 1×, thereby producing an electrophoretic protein sample. The protein extract sample (50 µg) was boiled for 5 minutes and then developed through 12.5% SDS-PAGE, and then stained with Coomassie Blue. In addition, the level of sGFP was identified by performing western blot analysis with an anti-GFP antibody. As a result, both of the expression vectors (pMEGR and pTEX1:sGFP) induced the expression of sGFP without separate co-infiltration of P38. However, when P38 was additionally co-infiltrated, higher sGFP expression was shown. In addition, both expression vectors showed almost the same level of sGFP expression. Through this, it was confirmed that even in the case of containing P38 by itself, more P38 is required for a sufficiently high level of gene silencing suppressor. Therefore, a construct that increases the expression of p38 contained in pTEX1 was reconstructed.

[Example 6] Expression Vector Maps of pTEX1, pTEX1N and pTEX1L

Since the expression of P38 contained in the pTEX1 did not provide sufficient gene silencing suppressors, it was attempted to construct a construct that increases the expression level of P38. 35S promoter-P38-35S terminator was obtained through PCR from pBIN based binary vector containing the nucleotide sequence of original TCV-CP, and the pTEX1N was constructed by substituting the corresponding fragment using BsrGI and Acc65I in pTEX1-EMCC. The pTEX1L was constructed by introducing L: P38 containing 5'-attattacatcaaaacaaaaa-3' (SEQ ID NO: 12), which is a nucleotide sequence capable of inducing high-efficiency translation, into the 5'-UTR of P38. Expression was identified by transformation into *Arabidopsis* protoplasts using pTEX1, pTEX1N and pTEX1L. After transformation, the protoplasts were incubated for 2 days at 28° C. in the LB plates containing kanamycin and rifampicin (50 mg/L and 100 mg/L, respectively). After selecting one colony, it was cultured overnight in the LB media containing 5 mL of kanamycin and rifampicin. Proteins were extracted from the protoplasts after 24 hours. Protein extract was prepared using an extraction buffer (50 mM Tris pH 7.5, 150 mM NaCl, 0.1% Triton X100, 2 mM DTT and 1% protease inhibitor cocktail), 5× sample buffer (250 mM Tris-HCl [pH 6.8], 10% SDS, 0.5% bromophenol blue, 50% glycerol v/v, and 500 mM DTT) was added thereto at a final concentration of 1×, thereby preparing an electrophoretic protein sample. The protein extract sample was boiled for 5 minutes, then separated through 10% SDS-PAGE, and then subject to western blot analysis using an anti-GFP antibody. Then, the membrane was stained with Coomassie Blue. As a result of comparing the expression levels of P38 after transforming the pTEX1, pTEX1N and pTEX1L into *Arabidopsis* protoplasts, the pTEX1 showed the lowest expression level, and it was confirmed that the pTEX1N expressed about twice as high as the pTEX1. On the other hand, the pTEX1L again showed twice higher expression than that of the pTEX1N ((D) in FIG. 6). Through this, it was confirmed that the expression vector containing the translational enhancer of the pTEX1L had the highest P38 expression level.

Example 7

A construct (pTEX1L:sGFP) containing M::BiP:sGFP:HDEL in the pTEX1L was constructed, and the level of expression was identified using the construct. The *Agrobacterium* delivering the vector containing a 35S promoter-sGFP-HSP terminator in the pCAMBIA1300 vector, the pMEGR vector and the pTEX1L vector was independently infiltrated into tobacco (*Nicotiana benthamiana*) leaves with a syringe, and also infiltrated simultaneously with p38. After infiltration, proteins were extracted from the tobacco leaves on the 5th day, and the expression of BiP-sGFP-HDEL and P38 proteins was identified by Western blot using a GFP antibody and a TCV CP antibody ((B) in FIG. 7). As a result, first, it was confirmed that in transient expression through agro-infiltration in tobacco, as in *Arabidopsis* protoplast transformation, the sGFP expression by the MacT promoter-RD29B termination site was two or three times higher than the expression by the 35S promoter-HSP terminator combination (FIG. 7). In addition, it was confirmed that there was no significant difference between the sGFP expression by the pMEGR with P38 co-infiltration and the sGFP expression by the pTEX1L:sGFP without P38 co-infiltration; also, there was almost no difference in the expression of sGFP even when pTEX1L:sGFP was co-transformed with P38. Through this, an expression vector for dual transfer was completed in which one binary vector can simultaneously transfer the target protein and p38, a gene silencing suppressor.

Example 8

By replacing the sGFP with a human Furin gene as the target gene in M::BiP:sGFP:HDEL in the pTEX1L, the construct in which the M::BiP:hFurin:Hisx5:HDEL construct was introduced into the pTEX1L was constructed. After introducing the construct into *Agrobacterium*, the expression was induced in *N. benthamiana*, thereby producing a high level of Furin:Hisx5:HDEL.

Example 9

By replacing the sGFP with Tryosinogen gene as the target gene in M::BiP:sGFP:HDEL in the pTEX1L, the construct in which the M::BiP:Trysinogen:Hisx5:HDEL construct was introduced into the pTEX1L was constructed. After introducing the construct into *Agrobacterium*, the expression was induced in *N. benthamiana*, thereby producing a high level of Trysinogen:Hisx5:HDEL.

The invention claimed is:

1. A recombinant vector for production of a target protein in a plant, comprising:
   (i) a Mac T promoter in which A, which is a 3' terminal base of a Mac promoter, is substituted with T;
   (ii) a gene coding a target protein; and
   (iii) a RD29B-t terminator.

2. The recombinant vector according to claim 1, wherein the sequence of the Mac promoter comprises the nucleotide sequence of SEQ ID NO: 1.

3. The recombinant vector according to claim 1, wherein the Mac T promoter comprises the nucleotide sequence of SEQ ID NO: 2.

4. The recombinant vector according to claim 1, wherein the RD29B-t terminator comprises the nucleotide sequence of SEQ ID NO: 3.

5. The recombinant vector according to claim 1, wherein the target protein is any one or more proteins selected from the group consisting of a soluble green fluorescent protein, an antigen, an antibody, an antibody fragment, a structural protein, a regulatory protein, a transcription factor, a toxin protein, a hormone, a hormone analog, a cytokine, an enzyme, an enzyme inhibitor, a transport protein, a receptor, a receptor fragment, a biodefense inducer, a storage protein, a movement protein, an exploitative protein, a growth factor, and a reporter protein.

6. The recombinant vector according to claim 1, wherein the vector is pCAMBIA1300.

7. The recombinant vector according to claim 1, wherein the recombinant vector further comprises a gene silencing suppressor gene.

8. The recombinant vector according to claim 7, wherein the gene silencing suppressor gene is any one or more selected from the group consisting of p38, P19, HC-Pro and TVA 2b.

9. A transformant transformed with the recombinant vector according to claim 1.

10. The transformant according to claim 9, wherein the transformant is *Agrobacterium*.

11. A method for producing a target protein in a plant, the method comprising the steps of:

(a) constructing the recombinant vector according to claim 1;

(b) introducing the recombinant vector into a cell to prepare a transformant;

(c) culturing the transformant;

(d) infiltrating the cultured transformant into the plant; and (e) pulverizing the plant to extract the target protein.

12. The method according to claim 11, wherein the step (d) further includes the step of infiltrating an additional transformant into the plant, wherein the additional transformant is prepared by introducing a recombinant vector containing p38 into a cell.

* * * * *